United States Patent [19]

Li et al.

[11] Patent Number: 5,118,359
[45] Date of Patent: Jun. 2, 1992

[54] METHOD OF CLEANING USING PARTIALLY FLUORINATED ALKANES HAVING A TERTIARY STRUCTURE AS SOLVENT

[75] Inventors: Chien C. Li, East Aurora, N.Y.; Bernard Sukornick, Cooper City, Fla.

[73] Assignee: Allied-Signal Inc., Morris Township, Morris County, N.J.

[21] Appl. No.: 718,137

[22] Filed: Jun. 20, 1991

Related U.S. Application Data

[62] Division of Ser. No. 546,067, Jun. 29, 1990, Pat. No. 5,059,728.

[51] Int. Cl.$^5$ ................................................. B08B 3/08
[52] U.S. Cl. ................................................ 134/42
[58] Field of Search ...................................... 134/42

[56] References Cited

U.S. PATENT DOCUMENTS 5,073,206   12/1991   Wilson et al. ............................ 134/42

*Primary Examiner*—Theodore Morris
*Assistant Examiner*—Zeinab El-Arini
*Attorney, Agent, or Firm*—Melanie L. Brown; Jay P. Friedenson

[57] ABSTRACT

Novel partially fluorinated alkanes having the Formula:

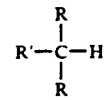

wherein each R is the same or different and is selected from the group consisting of $CF_3$, $CHF_2$, $CH_2F$, and $CH_3CF_2$, and R' is an alkyl or fluoroalkyl group having 1 to 6 carbon atoms with the proviso that when each R is $CF_3$, R' is not $CF_3(CF_2)_2-$, $CF_3CF_2-$, or $CF_3$ have utility as solvents in a variety of industrial cleaning applications including cold cleaning, dry cleaning, and defluxing of printed circuit boards.

14 Claims, No Drawings

METHOD OF CLEANING USING PARTIALLY FLUORINATED ALKANES HAVING A TERTIARY STRUCTURE AS SOLVENT

This application is a division of application Ser. No. 546,067, filed June 29, 1990, now U.S. Pat. No. 5,059,728.

FIELD OF THE INVENTION

This invention relates to novel partially fluorinated alkanes having a tertiary structure and 4 to 9 carbon atoms. These compounds are useful in a variety of vapor degreasing, cold cleaning, and solvent cleaning applications including defluxing and dry cleaning.

CROSS-REFERENCE TO RELATED APPLICATION

Commonly assigned concurrently filed patent application U.S. Ser. No. 546,173 claims a method for preparing foam using a partially fluorinated alkane having four or five carbon atoms and a tertiary structure as a blowing agent.

BACKGROUND OF THE INVENTION

Cold cleaning is an application where numerous solvents are used. In most cold cleaning applications, the soiled part is either immersed in the fluid or wiped with rags or similar objects soaked in solvents and allowed to air dry.

In cold cleaning applications, the use of the aerosol packaging concept has long been found to be a convenient and cost effective means of dispensing solvents. Aerosol products utilize a propellant gas or mixture of propellant gases, preferably in a liquified gas rather than a compressed gas state, to generate sufficient pressure to expel the active ingredients, i.e. Product concentrates such as solvents, from the container upon opening of the aerosol valve. The propellants may be in direct contact with the solvent, as in most conventional aerosol systems, or may be isolated from the solvent, as in barrier-type aerosol systems.

Vapor degreasing and solvent cleaning with fluorocarbon based solvents have found widespread use in industry for the degreasing and otherwise cleaning of solid surfaces, especially intricate parts and difficult to remove soils.

In its simplest form, vapor degreasing or solvent cleaning consists of exposing a room temperature object to be cleaned to the vapors of a boiling solvent. Vapors condensing on the object provide clean distilled solvent to wash away grease or other contamination. Final evaporation of solvent from the object leaves behind no residue as would be the case where the object is simply washed in liquid solvent.

For difficult to remove soils where elevated temperature is necessary to improve the cleaning action of the solvent, or for large volume assembly line operations where the cleaning of metal parts and assemblies must be done efficiently and quickly, the conventional operation of a vapor degreaser consists of immersing the part to be cleaned in a sump of boiling solvent which removes the bulk of the soil, thereafter immersing the part in a sump containing freshly distilled solvent near room temperature, and finally exposing the part to solvent vapors over the boiling sump which condense on the cleaned part. In addition, the part can also be sprayed with distilled solvent before final rinsing.

Vapor degreasers suitable in the above-describe operations are well known in the art. For example, Sherliker et al. in U.S. Pat. No. 3,085,918 disclose such suitable vapor degreasers comprising a boiling sump, a clean sump, a water separator, and other ancillary equipment.

Chlorofluorocarbon solvents, such as trichlorotrifluoroethane, have attained widespread use in recent years as effective, nontoxic, and nonflammable agents useful in degreasing applications and other solvent cleaning applications. One isomer of trichlorotrifluoroethane is 1,1,2-trichloro-1,2,2-trifluoroethane (known in the art as CFC-113). CFC-113 has a boiling point of about 47° C and has been found to have satisfactory solvent power for greases, oils, waxes and the like. It has therefore found widespread use for cleaning electric motors, compressors, heavy metal parts, delicate precision metal parts, printed circuit boards, gyroscopes, guidance systems, aerospace and missile hardware, aluminum parts and the like.

Another commonly used solvent is chloroform (known in the art as HCC-20) which has a boiling point of about 63° C. Perchloroethylene is a commonly used dry cleaning and vapor degreasing solvent which has a boiling point of about 121° C. These compounds are disadvantageous for use as solvents because they are toxic; also, chloroform causes liver damage when inhaled in excess.

Although chlorine is known to contribute to the solvency capability of a compound, fully halogenated chlorofluorocarbons and hydrochlorocarbons are suspected of causing environmental problems in connection with the earth's Protective ozone layer. Thus, the art is seeking new compounds which do not contribute to environmental problems but yet provide the solvency properties of CFC-113. From an environmental standpoint, hydrofluorocarbon and hydrocarbon Compounds are of interest because they are considered to be stratospherically safe substitutes for the currently used fully halogenated chlorofluorocarbons. Mathematical models have substantiated that hydrofluorocarbons and hydrocarbons will not adversely affect atmospheric chemistry as not contributing to ozone depletion and to green-house global warming in comparison to the fully halogenated species.

The problems with hydrofluorocarbons as solvents are that known straight chain hydrofluorocarbons such as $CH_3(CF_2)_4H$ and $CH_3CH_2(CF_2)_3H$ do not have the solvency power of CFC-113. A branched hydrofluorocarbon such as $CF_3CH(CF_3)_2$ is nonflammable but has a boiling point of about 15° C. and thus, is not liquid at room temperature at atmospheric pressure and is not useful in cold cleaning applications. The problems with hydrocarbons as solvents are that branched hydrocarbons such as isobutane are flammable and have such low boiling points that they are not liquid at room temperature and are not useful in cold cleaning applications. The problem with alkanols as solvents is that branched alkanols such as isobutanol are flammable.

It is an object of this invention to provide novel hydrofluorocarbon compounds which are liquid at room temperature and which are useful as solvents for use in vapor degreasing, cold cleaning, and other solvent cleaning applications including defluxing applications and dry cleaning.

Another object of the invention is to provide novel environmentally acceptable solvents for use in the aforementioned applications.

Other objects and advantages of the invention will become apparent from the following description.

DETAILED DESCRIPTION OF THE INVENTION

We have found a novel class of hydrofluorocarbons which we believe have good solvency characteristics. The present novel compounds are of the Formula:

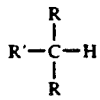

wherein each R is the same or different and is selected from the group consisting of $CF_3$, $CHF_2$, $CH_2F$, and $CH_3CF_2$—, and R' is an alkyl or fluoroalkyl group having 1 to 6 carbon atoms with the proviso that when each R is $CF_3$, R' is not $CF_3(CF_2)_2$—, $CF_2$—, or $CF_3$.

Because C in the Formula above has three alkyl groups thereon, these novel compounds have a tertiary structure. We believe that this tertiary structure provides good solvency power. The R component of the Formula above helps to make the hydrogen of the Formula above more acidic and therefore, more polar; thus, when the present compounds are used as solvents, the compounds have good solvency power for polar contaminants such as polyols and amines. The R' component of the Formula above helps to make the compounds nonpolar; thus, when the present compounds are used as solvents, the compounds also have good solvency power for nonpolar contaminants including hydrocarbons such as mineral oil. We also believe that these novel compounds have boiling points in the range of about 35 to about 80° C. which are comparable to those of CFC-113 and chloroform.

Preferably, R' in the Formula above is selected from the group consisting of $CF_3$, $CHF_2$, $CH_2F$, $CH_3$, $CF_3(CF_2)n$—, $CF_3CF_2CHF$—, $CF_3CF_2CH_2$—, $CF_3(CHF)n$—, $CF_3CHFCF_2$—, $CF_3CHFCH_2$—, $CF_3(CH_2)_n$—, $CF_3CH_2CF_2$—, $CF_3CH_2CHF$—, $CHF_2(CF_2)_n$—, $CHF_2CHFCF_2$—, $CHF_2CHFCH_2$—, $CHF_2(CHF)_n$—, $CHG_2CHFCF_2$—, $CHG_2CHFCH_2$—, $CHF_2(CH_2)_n$—, $CHF_2CH_2CF_2$—, $CHF_2CH_2CHF$—, $CH_2F(CF_2)_n$—, $CH_2FCF_2CHF$—, $CH_2FCF_2CH_2$—, $CH_2F(CHF)_n$—, $CH_2FCHFCF_2$—, $CH_2FCHFCH_2$—, $CH_2F(CH_2)_n$—, $CH_2FCH_2CF_2$—, $CH_2FCH_2CHF$—, $CH_3(CF_2)_n$—, $CH_3CHFCF_2$—, $CH_3CF_2CH_2$—, $CH_3(CHF)_n$—, $CH_3CHFCF_2$—, $CH_3CHFCH_2$—, and $CH_3(CH_2)_m(CF_2)_n$, and m is 1 to 3, and n is 1 or 2 with the proviso that when each R is $CF_3$, R' is not $CF_3$, $CF_3CF_2$—, or $CF_3(CF_2)_2$—.

In the Formula above, when one R is $CF_3$, the other R is $CHG_2$, and R' is $CH_3$, the compound is 2-methyl-1,1,1,3,3-pentafluoropropane. When one R is $CF_3$, the other R is $CH_2F$, and R' is $CH_3$, the compound is 2-methyl-1,1,1,3-tetrafluoropropane. When one R is $CF_3$, the other R is $CH_2F$, and R' is $CHG_2CHF$—, the compound is 2-fluoromethyl-1,1,1,3,4,4-hexafluorobutane. When one R is $CF_3$, the other R is $CH_3CF_2$—, and R' is $CH_3$, the compound is 2-methyl-1,1,1,3,3-pentafluorobutane. When one R is $CHG_2$, the other R is $CH_2F$, and R' is $CH_3$, the compound is 2-methyl-1,1,3-trifluoropropane. When one R is $CHG_2$, the other R is $CH_2F$, and R' is $CHF_2CH_2$—, the compound is 2-fluoromethyl-1,1,4,4-tetrafluorobutane.

The present novel compounds may be prepared by adapting known methods for preparing hydrofluorocarbons. For example, 2-methyl-1,1,1,3,3-pentafluoropropane may be prepared by reacting commercially available 1,1,1-trifluoro-2-propanone with $CF_2$ carbane to form 2-trifluoromethyl-1,1-difluoro-1-propene which may then be hydrogenated to form 2-methyl-1,1,1,3,3-pentafluoropropane.

As another example, 2-methyl-1,1,1,3-tetrafluoropropane may be prepared by reacting commercially available methacrylic acid with hydrogen fluoride to form 2-methyl-3-fluoropropanoic acid which may then be fluorinated to form 2-methyl-1,1,1,3-tetrafluoropropane.

As another example, 2-fluoromethyl-1,1,1,3,4,4-hexafluorobutane may be prepared by fluorinating commercially available 3-chloropropionic acid to form 1,1,1,3-tetrafluoropropane which may then be reacted with $CHG_2CF$ carbene to form 2-fluoromethyl-1,1,1,3,4,4-hexafluorobutane.

As another example, 2-methyl-1,1,1,3,3-pentafluorobutane may be prepared by fluorinating commercially available 2-methyl-1-buten-3-yne to form 3-methyl-1,2,3,4-tetrafluoro-1-butene which may then be reacted with hydrogen fluoride to form 2-methyl-1,2,3,3,4-pentafluorobutane. The 2-methyl-1,2,3,3,4-pentafluorobutane may then be dehalogenated to form 3-methyl-2,3,4-trifluoro-1-butene which may then be reacted with hydrogen fluoride to form 2-methyl-1,2,3,3-tetrafluorobutane. The 2-methyl-1,2,3,3-tetrafluorobutane may then be dehalogenated to form 2-methyl-1,3,3-trifluoro-1-butene which may then be fluorinated to form 2-methyl-1,1,2,3,3-pentafluorobutane. The 2-methyl-1,1,2,3,3-pentafluorobutane may then be dehydrohalogenated to form 2-methyl-1,1,3,3-tetrafluoro-1-butene which may then be reacted with hydrogen fluoride to form 2-methyl-1,1,1,3,3-pentafluorobutane. The boiling point of 2-methyl-1,1,1,3,3-pentafluorobutane is calculated to be about 60° C. Because of its boiling point, 2-methyl-1,1,1,3,3-pentafluorobutane would be particularly useful as a solvent substitute for chloroform.

For example, 2-methyl-1,1,3-trifluoropropane may be prepared by reacting commercially available fluoroacetone with a $CF_2$ carbene to form 2-fluoromethyl-1,1,3-trifluoro-1-propene which may then be hydrogenated to form 2-methyl-1,1,3-trifluoropropane.

As another example, 2-fluoromethyl-1,1,4,4-tetrafluorobutane may be prepared by oxidizing commercially available 3-fluoro-1,2-propanediol to form a product which may then be reacted with $CF_2$ carbene to form 2-fluoromethyl-1,1,4,4-tetrafluoro-1,3-butadiene which may then be hydrogenated to form 2-fluoromethyl-1,1,4,4-tetrafluorobutane.

Preferably, each R in the formula above is the same. When each R is $CHG_2$ and R' is $CF_3$, the compound is 2-difluoromethyl-1,1,1,3,3-pentafluoropropane. When each R is $CHG_2$ and R' is $CHG_2$, the compound is 2-difluoromethyl-1,1,3,3-tetrafluoropropane. When each R is $CHG_2$ and R' is $CH_2F$, the compound is 2-fluoromethyl-1,1,3,3-tetrafluoropropane. When each R is $CHF_2$ and R' is $CH_3$, the compound is 2-methyl-1,1,3,3-tetrafluoropropane. When each R is $CH_2F$ and R' is $CHF_2$, the compound is 2-fluoromethyl-1,1,3-trifluoropropane. When each R is $CH_2F$ and R' is $CH_2F$, the compound is 2-fluoromethyl-1,3-difluoropropane. When each R is $CH_3CF_2$— and R' is $CF_3$, the compound is 3-trifluoromethyl-2,2,4,4-tetrafluoropentane.

As another preparation example, 2-difluoromethyl-1,1,1,3,3-pentafluoropropane may be prepared by fluorinating commercially available 1,1,1,3,3-pentachloro-2-propanone to form 1,1,1,3,3-pentafluoro-2-propanone which may then be reacted with $CF_2$ carbene to form 2-difluoromethyl-1,1,3,3,3-tetrafluoro-1-propene. The 2-difluoromethyl-1,1,3,3,3-tetrafluoro-1-propene may then be hydrogenated to form 2-difluoromethyl-1,1,1,3,3-pentafluoropropane.

As another example, the 2-difluoromethyl-1,1,3,3-tetrafluoropropane may be prepared by fluorinating commercially available 1,1,3-trichloro-2-propanone to form 1,1,3-trifluoro-2-propanone which may then be reacted with $CF_2$ carbene to form 2-fluoromethyl-1,1,3,3-tetrafluoro-1-propene. The 2-fluoromethyl-1,1,3,3-tetrafluoro-1-propene may then be hydrogenated to form 2-fluoromethyl-1,1,3,3-tetrafluoropropane. The 2-fluoromethyl-1,1,3,3-tetrafluoropropane may then be dehydrogenated to form 2-difluoromethyl-1,3,3-trifluoro-1-propene which may then be reacted with hydrogen fluoride to form 2-difluoromethyl-1,1,3,3-tetrafluoropropane.

As another example, 2-fluoromethyl-1,1,3,3-tetrafluoropropane may be prepared by fluorinating commercially available 1,1,3-trichloro-2-propanone to form 1,1,3-trifluoro-2-Propanone which may then be reacted with $CF_2$ carbene to form 2-fluoromethyl-1,1,3,3-tetrafluoro-1-propene. The 2-fluoromethyl-1,1,3,3-tetrafluoro-1-propene may then be hydrogenated to form 2-fluoromethyl-1,1,3,3-tetrafluoropropane.

As another example, 2-methyl-1,1,3,3-tetrafluoropropane may be prepared by fluorinating commercially available 1,1-dichloro-2-propanone to form 1,1-difluoro-2-propanone which may then be reacted with $CF_2$ carbene to form 2-methyl-1,1,3,3-tetrafluoro-1-propene. The 2-methyl-1,1,3,3-tetrafluoro-1-propene may then be hydrogenated to form 2-methyl-1,1,3,3-tetrafluoropropane.

As another example, the 2-fluoromethyl-1,1,3-trifluoropropane may be prepared by oxidizing commercially available 1,3-difluoro-2-propanol to 1,3-difluoro-2-propanone which may then be reacted with a $CF_2$ carbene to form 2-fluoromethyl-1,1,3-trifluoro-1-propene. The 2-fluoromethyl-1,1,3-trifluoro-1-propene may then be hydrogenated to form 2-fluoromethyl-1,1,3-trifluoropropane.

As another example, the 2-fluoromethyl-1,3-difluoropropane may be prepared by oxidizing commercially available 1,3-difluoro-2-propanol to 1,3-difluoro-2-propanone which may then be reacted with a $CF_2$ carbene to form 2-fluoromethyl-1,1,3-trifluoro-1-propene. The 2-fluoromethyl-1,1,3-trifluoro-1-propene may then be hydrogenated to form 2-fluoromethyl-1,1,3-trifluoropropane. The 2-fluoromethyl-1,1,3-trifluoropropane may then be dehydrohalogenated to form 2-fluoromethyl-1,3-difluoro-1-propene which may then be hydrogenated to form 2-fluoromethyl-1,3-difluoropropane.

As another example, the 3-trifluoromethyl-2,2,4,4-tetrafluoropentane may be prepared by fluorinating commercially available 2,4-pentanedione to form 2,2,4,4-tetrafluoropentane which may then be dehydrohalogenated to form 2,4,4-trifluoro-2-pentene. The 2,4,4-trifluoro-2-pentene may then be reacted with $CF_3$ to form 3-trifluoromethyl-2,2,4,4-tetrafluoropentane.

The boiling point of 2-difluoromethyl-1,1,3,3-tetrafluoropropane is calculated to be about 61° C. while the boiling point of 2-fluoromethyl-1,3-difluoropropane is calculated to be about 51° C. The boiling point of 3-trifluoromethyl-2,2,4,4-tetrafluoropentane is calculated to be about 52° C.

Because of its boiling point, 2-difluoromethyl-1,1,3,3-tetrafluoropropane would be particularly useful as a solvent substitute for chloroform. Because of their boiling points, 2-fluoromethyl-1,3-difluoropropane and 3-trifluoromethyl-2,2,4,4-tetrafluoropentane would be particularly useful as solvent substitutes for CFC-113.

More preferably, each R in the Formula above is $CF_3$. When R' is $CF_3CF_2CHF-$, the compound is 2-trifluoromethyl-1,1,1,3,4,4,5,5,5-nonafluoropentane.

To prepare 2-trifluoromethyl-1,1,1,3,4,4,5,5,5-nonafluoropentane, commercially available hexafluoropropene may be oligomerized with commercially available trimethylamine in a dipolar aprotic solvent such as commercially available tetrahydrofuran to provide $(CF_3)_2C:CFCF_2CF_3$ as taught by W. Brunskill et al., "Anionic Oligomerisation of Hexafluoropropene: Fission of a Carbon-Carbon Bond by Fluoride Ion", *Chemical Communications*, 1444 (1970); the $(CF_3)_2C:CFCF_2CF_3$ may then be hydrogenated to form 2-trifluoromethyl-1,1,1,3,4,4,5,5,5-nonafluoropentane.

Most preferably, each R is $CF_3$ and R' is selected from the group consisting of $CHF_2$, $CH_3$, $CF_3CHF-$, $CF_3CH_2-$, $CHF_2CH_2-CH_3CF_2-$, $CH_3(CF_2)_2-$, $CH_3CH_2CF_2-$, and $CH_3CH_2CF_2CF_2-$. The names of the preceding preferred hydrofluorocarbons are 2-difluoromethyl-1,1,1,3,3,3-hexafluoropropane; 2-methyl-1,1,1,3,3,3-hexafluoropropane; 2-trifluoromethyl-1,1,1,3,4,4,4-heptafluorobutane; 2-trifluoromethyl-1,1,1,4,4,4-hexafluorobutane; 2-trifluoromethyl-1,1,1,4,4-pentafluorobutane; 2-trifluoromethyl-1,1,1,3,3-pentafluorobutane; 2-trifluoromethyl-1,1,1,3,3,4,4-heptafluoropentane; 2-trifluoromethyl-1,1,1,3,3-pentafluoropentane; and 2-trifluoromethyl-1,1,1,3,3,4,4-heptafluorohexane.

The present novel compounds may be prepared by adapting known methods for preparing hydrofluorocarbons. For example, 2-difluoromethyl-1,1,1,3,3,3-hexafluoropropane may be prepared by treating commercially available hexafluoropropene with hydrogen fluoride as taught by commonly assigned U.K. Patent 902,590 to form 1,1,1,2,3,3,3-hexafluoropropane. The 1,1,1,2,3,3,3-hexafluoropropane may then be heated at 475–700° C. in the presence of activated carbon as taught by commonly assigned U.S. Pat. No. 2,981,763 which is incorporated herein by reference to form 2-trifluoromethyl-1,1,1,3,3,3-hexafluoropropane or nonafluoroisobutane. The nonafluoroisobutane may then be treated with commercially available benzoyl chloride in the presence of commercially available triethylamine as taught by B. L. Dyatkin et al., "The Perfluoro-t-butyl Anion in the Synthesis of Organofluorine Compounds", *Russian Chemical Reviews* 45(7), 607 (1976) to form perfluoroisobutene. The perfluoroisobutene may then by hydrogenated to form 2-difluoromethyl-1,1,1,3,3,3-hexafluoropropane.

As another example, 2-methyl-1,1,1,3,3,3-hexafluoropropane may be prepared by reacting commercially available hexafluoropropene with elemental sulfur and commercially available potassium fluoride in commercially available dimethylformamide under substantially atmospheric pressure and at temperatures between 25-100° C. as taught by commonly assigned U.S. Pat. No. 4,326,068 which is incorporated herein by reference to form hexafluorothioacetone dimer. The hexafluorothioacetone dimer may then be reacted with commercially available formaldehyde as taught by commonly assigned U.S. Pat. No. 4,367,349 which is incorporated herein by reference to form hexafluoroisobutylene. The hexafluoroisobutylene may then be hydrogenated to form 2-methyl-1,1,1,3,3,3-hexafluoropropane.

As another example, 2-trifluoromethyl-1,1,1,3,4,4,4-heptafluorobutane may be prepared by reacting commercially available 1,1-difluoroethylene according to the procedure of George L. Fleming et al., "Addition of Free Radicals to Unsaturated Systems. Part XX. The Direction of Radical Addition of Heptafluoro-2-iodopropane to Vinyl Fluoride, Trifluoroethylene, and Hexafluoropropene", *J. C. S. Perkin I*, 574 (1973) to form a product which may then be fluorinated to form 2-trifluoromethyl-1,1,1,2,3,4,4,4-octafluorobutane. The 2-trifluoromethyl-1,1,1,2,3,4,4,4-octafluorobutane may then be dehydrohalogenated and then hydrogenated to form 2-trifluoromethyl-1,1,1,3,4,4,4-heptafluorobutane.

As another example, 2-trifluoromethyl-1,1,1,4,4,4-hexafluorobutane may be prepared by reacting commercially available 1,1-difluoroethylene according to the procedure of George L. Fleming et al., supra, to form a product which may then be reacted with hydrogen fluoride to form 2-trifluoromethyl-1,1,1,2,4,4,4-hexafluorobutane which may then be dehydrohalogenated and then hydrogenated to form 2-trifluoromethyl-1,1,1,4,4,4-hexafluorobutane.

As another example, 2-trifluoromethyl-1,1,1,4,4-pentafluorobutane may be prepared by reacting commercially available 1,1-difluoroethylene according to the procedure of George L. Fleming et al., supra, to form a product which may then be hydrogenated to form 2-trifluoromethyl-1,1,1,2,4,4-hexafluorobutane which may then be dehydrohalogenated and then hydrogenated to form 2-trifluoromethyl-1,1,1,4,4-pentafluorobutane.

As another example, 2-trifluoromethyl-1,1,1,3,3-pentafluorobutane may be prepared by fluorinating commercially available 2-butanone to form 2,2-difluorobutane which may then be dehydrogenated to form 3,3-difluoro-1-butene. $CF_3$ may then be added to the 3,3-difluoro-1-butene to form 2-trifluoromethyl-1,3,3-trifluorobutane which may then be dehydrogenated to form 2-trifluoromethyl-1,3,3-trifluoro-1-butene. The 2-trifluoromethyl-1,3,3-trifluoro-1-butene may then be reacted with hydrogen fluoride to form 2-difluoromethyl-1,1,1,3,3-hexafluorobutane which may then be dehydrogenated to form 2-trifluoromethyl-1,1,3,3-tetrafluoro-1-butene which may then be reacted with hydrogen fluoride to form 2-trifluoromethyl-1,1,1,3,3-pentafluorobutane.

As another example, 2-trifluoromethyl-1,1,1,3,3,4,4-heptafluoropentane may be prepared by fluorinating commercially available 2,3-pentanedione to form 2,2,3,3-tetrafluoropentane which may then be dehydrogenated to form 3,3,4,4-tetrafluoro-1-pentene. $CF_3$ may then be added to the 3,3,4,4-tetrafluoro-1-pentene to form 2-trifluoromethyl-1,3,3,4,4-pentafluoropentane which may then be dehydrogenated to form 2-trifluoromethyl-1,3,3,4,4-pentafluoro-1-pentene. The 2-trifluoromethyl-1,3,3,4,4-pentafluoro-1-pentene may then be reacted with hydrogen fluoride to form 2-trifluoromethyl-1,1,3,3,4,4-hexafluoropentane which may then be dehydrogenated to form 2-trifluoromethyl-1,1,3,3,4,4-hexafluoro-1-pentene which may then be reacted with hydrogen fluoride to form 2-trifluoromethyl-1,1,1,3,3,4,4-heptafluoropentane.

As another example, 2-trifluoromethyl-1,1,1,3,3-pentafluoropentane may be prepared by fluorinating 3-pentanone to form 3,3-difluoropentane which may then be dehydrogenated to form 3,3-difluoro-1-pentene. $CF_3$ may then be reacted with the 3,3-difluoro-1-pentene to form 2-trifluoromethyl-1,3,3-trifluoropentane which may then be dehydrogenated to form 2-trifluoromethyl-1,3,3-trifluoro-1-pentene. The 2-trifluoromethyl-1,3,3-trifluoro-1-pentene may then be reacted with hydrogen fluoride to form 2-trifluoromethyl-1,1,3,3-tetrafluoropentane which may then be dehydrogenated to form 2-trifluoromethyl-1,1,3,3-tetrafluoro-1-pentene which may then be reacted with hydrogen fluoride to form 2-trifluoromethyl-1,1,1,3,3-pentafluoropentane.

As another example, 2-trifluoromethyl-1,1,1,3,3,4,4-heptafluorohexane may be prepared by fluorinating commercially available 3,4-hexanedione to form 3,3,4,4-tetrafluorohexane which may then be dehydrogenated to form 3,3,4,4-tetrafluoro-1-hexene. $CF_3$ may then be added to the 3,3,4,4-tetrafluoro-1-hexene to form 2-trifluoromethyl-1,3,3,4,4-pentafluorohexane which may then be dehydrogenated to form 2-trifluoromethyl-1,3,3,4,4-pentafluoro-1-hexene. The 2-trifluoromethyl-1,3,3,4,4-pentafluoro-1-hexene may then be reacted with hydrogen fluoride to form 2-trifluoromethyl-1,1,3,3,4,4-hexafluorohexane which may then be dehydrogenated to form 2-trifluoromethyl-1,1,3,3,4,4-hexafluoro-1-hexene which may then be reacted with hydrogen fluoride to form 2-trifluoromethyl-1,1,1,3,3,4,4-heptafluorohexane.

The boiling point of 2-difluoromethyl-1,1,1,3,3,3-hexafluoropropane is calculated to be about 38° C while the boiling point of 2-methyl-1,1,1,3,3,3-hexafluoropropane is calculated to be about 30° C. The boiling point of 2-trifluoromethyl-1,1,1,4,4,4-hexafluorobutane is calculated to be about 75° C. The boiling point of 2-trifluoromethyl-1,1,1,3,3-pentafluoropentane is calculated to be about 38° C. while the boiling point of 2-trifluoromethyl-1,1,1,3,3,4,4-heptafluorohexane is calculated to be about 55° C.

The present novel compounds are useful as solvents in a variety of vapor degreasing, cold cleaning, and solvent cleaning applications including defluxing and dry cleaning. Because of their boiling points, 2-difluoromethyl-1,1,1,3,3,3-hexafluoropropane, 2-methyl-1,1,1,3,3,3-hexafluoropropane, 2-trifluoromethyl-1,1,1,3,3-pentafluoropentane, and 2-trifluoromethyl-1,1,1,3,3,4,4-heptafluorohexane would be useful as solvent substitutes for CFC-113. Because of its boiling point, 2-trifluoromethyl-1,1,1,4,4,4-hexafluorobutane would be particularly useful as a solvent substitute for chloroform and perchloroethylene.

The present invention also provides a method of cleaning a solid surface which comprises treating the surface with a compound having the Formula:

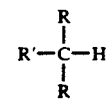

wherein each R is the same or different and is selected from the group consisting of $CF_3$, $CHF_2$, $CH_2F$, and $CH_3CF_2$, and R' is an alkyl or fluoroalkyl group having 1 to 6 carbon atoms.

Preferably, R' in the Formula above is selected from the group consisting of $CF_3$, $CHF_2$, $CH_2F$, $CH_3$, $CF_3(CF_2)_n-$, $CF_3CF_3CF_2CHF-$, $CF_3CF_2CH_2-$, $CF_3(CHF)_n-$, $CF_3CHFCF_2-$, $CF_3CHFCH_2-$, $CF_3(CH_2)_n$—, $CF_3CH_2CF_2$—, $CF_3CH_2CHF$—, $CHF_2(CF_2)_n$—, $CHF_2CF_2CHF$—, $CHF_2CF_2CH_2$—, $CHF_2(CHF)_n$—, $CHF_2CHFCF_2$—, $CHF_2CHFCH_2$—, $CHF_2(CH_2)_n$—, $CHF_2CH_2CF_2$—, $CHF_2CH_2CHF$—, $CH_2F(CF_2)_n$—, $CH_2FCF_2CHF$—, $CH_2FCF_2CH_2$—, $CH_2F(CHF)_n$—, $CH_2FCHFCF_2$—, $CH_2FCHFCH_2$—, $CH_2F(CH_2)_n$—, $CH_2FCH_2CF_2$—, $CH_2FCH_2CHF$—, $CH_3(CF_2)_n$—, $CH_3CF_2CHF$—, $CH_3CF_2CH_2$—, $CH_3(CHF)_n$—, $CH_3CHFCF_2$—, $CH_3CHFCH_2$—, and $CH_3(CF_2)_m(CF_2)_n$, and m is 1 to 3, and n is 1 or 2.

Preferably, each R in the Formula above is the same and more preferably, each R in the Formula above is $CF_3$ When R' is $CF_3CF_2CF_2$—, the compound is 2-trifluoromethyl-1,1,1,3,3,4,4,5,5,5-decafluoropentane. To prepare 2-trifluoromethyl-1,1,1,3,3,4,4,5,5,5-decafluoropentane, any method known in the art may be used. For example, commercially available hexafluoropropene may be oligomerized with commercially available trimethylamine in a dipolar aprotic solvent such as commercially available tetrahydrofuran to provide $(CF_3)_2C:CFCF_2CF_3$ which is then reacted with commercially available hydrogen fluoride to yield 2-trifluoromethyl-1,1,1,3,3,4,4,5,5,5-decafluoropentane as taught by W. Brunskill et al., "Anionic Oligomerisation of Hexafluoropropene: Fission of a Carbon-Carbon Bond by Fluoride Ion", *Chemical Communications*, 1444 (1970).

When R' is $CF_3CF_2$—, the compound is 2-trifluoromethyl- 1,1,1,3,3,4,4,4-octafluorobutane. To prepare 2-trifluoromethyl-1,1,1,3,3,4,4,4-octafluorobutane, any method known in the art may be used. For example, 2-trifluoromethyl-1,1,1,3,3,4,4,4-octafluorobutane may be prepared by reacting caesium fluoride and perfluoro-3-methylbutlene in moist sulpholan as taught by Robert N. Haszeldine et al., "Fluoro-olefin Chemistry. Part 11. Some Reactions of Perfluoro-3-methylbut-1-ene under Ionic and Free-radical Conditions", *J. Chem. Soc.* 565 (1979).

When R' is $CF_3$, the compound is 2-trifluoromethyl-1,1,1,3,3,3-hexafluoropropane To prepare 2-trifluoromethyl-1,1,1,3,3,3-hexafluoropropane, any method known in the art may be used. For example, commercially available hexafluoropropene may be reacted with hydrogen fluoride to form 1,1,1,2,3,3,3-heptafluoropropane which may then be heated at about 475–700° C. in the presence of activated carbon to form 2-trifluoromethyl-1,1,1,3,3,3-hexafluoropropane as taught by commonly assigned U.S. Pat. No. 2,981,763 which is incorporated herein by reference.

The boiling point of 2-trifluoromethyl-1,1,1,3,3,4,4,4-octafluorobutane is calculated to be about 47° C. Because of its boiling Point, 2-trifluoromethyl-1,1,1,3,3,4,4,4-octafluorobutane would be particularly useful as a solvent substitute for CFC-113.

In the process embodiment of the invention, the compositions may be used to clean solid surfaces by treating the surfaces with the compounds in any manner well known to the art such as by dipping or spraying or use of conventional degreasing apparatus.

When the novel compounds are used to clean solid surfaces by spraying the surfaces with the compounds, preferably, the novel compounds are sprayed onto the surfaces by using a propellant. Preferably, the propellant is selected from the group consisting of hydrochlorofluorocarbon, hydrofluorocarbon, and mixtures thereof. Useful hydrochlorofluorocarbon propellants include dichlorofluoromethane (known in the art as HCFC-21), chlorodifluoromethane (known in the art as HCFC-22), 1,1-dichloro-2,2-difluoroethane (known in the art as HCFC-132a), 1-chloro-2,2,2-trifluoroethane (known in the art as HCFC-133), and 1-chloro-1,1-difluoroethane (known in the art as HCFC-142b); commercially available HCFC-21, HCFC-22, and HCFC-142b may be used in the present invention. Useful hydrofluorocarbon propellants include trifluoromethane (known in the art as HFC-23), 1,1,1,2-tetrafluoroethane (known in the art as HFC-134a), and 1,1-difluoroethane (known in the art as HFC-152a); commercially available HFC-23 and HFC-152a may be used in the present invention. Until HFC-134a becomes available in commercial quantities, HFC-134a may be made by a known method such as that disclosed by U.S. Pat. No. 4,851,595. Preferred propellants include chlorodifluoromethane and 1,1,1,2-tetrafluoroethane.

The present partially fluorinated alkanes may also be used as blowing agents for preparing foam as disclosed in commonly assigned concurrently filed patent application U.S. Ser. No. 546,173, which is incorporated herein by reference.

The present invention is more fully illustrated by the following non-limiting Examples.

EXAMPLES 1–540

For each example, the novel compound of the Formula above having the R and R' groups as indicated in Table I below is made.

TABLE I

| Example | R | R' |
|---|---|---|
| 1 | $CF_3$, $CHF_2$ | $CF_3$ |
| 2 | $CF_3$, $CHF_2$ | $CHF_2$ |
| 3 | $CF_3$, $CHF_2$ | $CH_2F$ |
| 4 | $CF_3$, $CHF_2$ | $CH_3$ |
| 5 | $CF_3$, $CHF_2$ | $CF_3CF_2$ |
| 6 | $CF_3$, $CHF_2$ | $CF_3(CF_2)_2$ |
| 7 | $CF_3$, $CHF_2$ | $CF_3CF_2CHF$ |
| 8 | $CF_3$, $CHF_2$ | $CF_3CF_2CH_2$ |
| 9 | $CF_3$, $CHF_2$ | $CF_3CHF$ |
| 10 | $CF_3$, $CHF_2$ | $CF_3(CHF)_2$ |
| 11 | $CF_3$, $CHF_2$ | $CF_3CHFCF_2$ |
| 12 | $CF_3$, $CHF_2$ | $CF_3CHFCH_2$ |
| 13 | $CF_3$, $CHF_2$ | $CF_3CH_2$ |
| 14 | $CF_3$, $CHF_2$ | $CF_3(CH_2)_2$ |
| 15 | $CF_3$, $CHF_2$ | $CF_3CH_2CF_2$ |
| 16 | $CF_3$, $CHF_2$ | $CF_3CH_2CHF$ |
| 17 | $CF_3$, $CHF_2$ | $CHF_2CF_2$ |
| 18 | $CF_3$, $CHF_2$ | $CHF_2(CF_2)_2$ |
| 19 | $CF_3$, $CHF_2$ | $CHF_2CF_2CHF$ |
| 20 | $CF_3$, $CHF_2$ | $CHF_2CF_2CH_2$ |
| 21 | $CF_3$, $CHF_2$ | $CHF_2CHF$ |
| 22 | $CF_3$, $CHF_2$ | $CHF_2(CHF)_2$ |
| 23 | $CF_3$, $CHF_2$ | $CHF_2CHFCF_2$ |
| 24 | $CF_3$, $CHF_2$ | $CHF_2CHFCH_2$ |
| 25 | $CF_3$, $CHF_2$ | $CHF_2CH_2$ |
| 26 | $CF_3$, $CHF_2$ | $CHF_2(CH_2)_2$ |
| 27 | $CF_3$, $CHF_2$ | $CHF_2CH_2CF_2$ |
| 28 | $CF_3$, $CHF_2$ | $CHF_2CH_2CHF$ |
| 29 | $CF_3$, $CHF_2$ | $CH_2FCF_2$ |
| 30 | $CF_3$, $CHF_2$ | $CH_2F(CF_2)_2$ |
| 31 | $CF_3$, $CHF_2$ | $CH_2FCF_2CHF$ |
| 32 | $CF_3$, $CHF_2$ | $CH_2FCF_2CH_2$ |
| 33 | $CF_3$, $CHF_2$ | $CH_2FCHF$ |
| 34 | $CF_3$, $CHF_2$ | $CH_2F(CHF)_2$ |
| 35 | $CF_3$, $CHF_2$ | $CH_2FCHFCF_2$ |
| 36 | $CF_3$, $CHF_2$ | $CH_2FCHFCH_2$ |
| 37 | $CF_3$, $CHF_2$ | $CH_2FCH_2$ |
| 38 | $CF_3$, $CHF_2$ | $CH_2F(CH_2)_2$ |
| 39 | $CF_3$, $CHF_2$ | $CH_2FCH_2CF_2$ |
| 40 | $CF_3$, $CHF_2$ | $CH_2FCH_2CHF$ |
| 41 | $CF_3$, $CHF_2$ | $CH_3CF_2$ |
| 42 | $CF_3$, $CHF_2$ | $CH_3(CF_2)_2$ |
| 43 | $CF_3$, $CHF_2$ | $CH_3CF_2CHF$ |
| 44 | $CF_3$, $CHF_2$ | $CH_3CF_2CH_2$ |
| 45 | $CF_3$, $CHF_2$ | $CH_3CHF$ |
| 46 | $CF_3$, $CHF_2$ | $CH_3(CHF)_2$ |

TABLE I-continued

| Example | R | R' |
|---|---|---|
| 47 | CF$_3$, CHF$_2$ | CH$_3$CHFCF$_2$ |
| 48 | CF$_3$, CHF$_2$ | CH$_3$CHFCH$_2$ |
| 49 | CF$_3$, CHF$_2$ | CH$_3$CH$_2$CF$_2$ |
| 50 | CF$_3$, CHF$_2$ | CH$_3$CH$_2$(CF$_2$)$_2$ |
| 51 | CF$_3$, CHF$_2$ | CH$_3$(CH$_2$)$_2$CF$_2$ |
| 52 | CF$_3$, CHF$_2$ | CH$_3$(CH$_2$)$_2$(CF$_2$)$_2$ |
| 53 | CF$_3$, CHF$_2$ | CH$_3$(CH$_2$)$_3$CF$_2$ |
| 54 | CF$_3$, CHF$_2$ | CH$_3$(CH$_2$)$_3$(CF$_2$)$_2$ |
| 55 | CF$_3$, CH$_2$F | CF$_3$ |
| 56 | CF$_3$, CH$_2$F | CHF$_2$ |
| 57 | CF$_3$, CH$_2$F | CH$_2$F |
| 58 | CF$_3$, CH$_2$F | CH$_3$ |
| 59 | CF$_3$, CH$_2$F | CF$_3$CF$_2$ |
| 60 | CF$_3$, CH$_2$F | CF$_3$(CF$_2$)$_2$ |
| 61 | CF$_3$, CH$_2$F | CF$_3$CF$_2$CHF |
| 62 | CF$_3$, CH$_2$F | CF$_3$CF$_2$CH$_2$ |
| 63 | CF$_3$, CH$_2$F | CF$_3$CHF |
| 64 | CF$_3$, CH$_2$F | CF$_3$(CHF)$_2$ |
| 65 | CF$_3$, CH$_2$F | CF$_3$CHFCF$_2$ |
| 66 | CF$_3$, CH$_2$F | CF$_3$CHFCH$_2$ |
| 67 | CF$_3$, CH$_2$F | CF$_3$CH$_2$ |
| 68 | CF$_3$, CH$_2$F | CF$_3$(CH$_2$)$_2$ |
| 69 | CF$_3$, CH$_2$F | CF$_3$CH$_2$CF$_2$ |
| 70 | CF$_3$, CH$_2$F | CF$_3$CH$_2$CHF |
| 71 | CF$_3$, CH$_2$F | CHF$_2$CF$_2$ |
| 72 | CF$_3$, CH$_2$F | CHF$_2$(CF$_2$)$_2$ |
| 73 | CF$_3$, CH$_2$F | CHF$_2$CF$_2$CHF |
| 74 | CF$_3$, CH$_2$F | CHF$_2$CF$_2$CH$_2$ |
| 75 | CF$_3$, CH$_2$F | CHF$_2$CHF |
| 76 | CF$_3$, CH$_2$F | CHF$_2$(CHF)$_2$ |
| 77 | CF$_3$, CH$_2$F | CHF$_2$CHFCF$_2$ |
| 78 | CF$_3$, CH$_2$F | CHF$_2$CHFCH$_2$ |
| 79 | CF$_3$, CH$_2$F | CHF$_2$CH$_2$ |
| 80 | CF$_3$, CH$_2$F | CHF$_2$(CH$_2$)$_2$ |
| 81 | CF$_3$, CH$_2$F | CHF$_2$CH$_2$CF$_2$ |
| 82 | CF$_3$, CH$_2$F | CHF$_2$CH$_2$CHF |
| 83 | CF$_3$, CH$_2$F | CH$_2$FCF$_2$ |
| 84 | CF$_3$, CH$_2$F | CH$_2$F(CF$_2$)$_2$ |
| 85 | CF$_3$, CH$_2$F | CH$_2$FCF$_2$CHF |
| 86 | CF$_3$, CH$_2$F | CH$_2$FCF$_2$CH$_2$ |
| 87 | CF$_3$, CH$_2$F | CH$_2$FCHF |
| 88 | CF$_3$, CH$_2$F | CH$_2$F(CHF)$_2$ |
| 89 | CF$_3$, CH$_2$F | CH$_2$FCHFCF$_2$ |
| 90 | CF$_3$, CH$_2$F | CH$_2$FCHFCH$_2$ |
| 91 | CF$_3$, CH$_2$F | CH$_2$FCH$_2$ |
| 92 | CF$_3$, CH$_2$F | CH$_2$F(CH$_2$)$_2$ |
| 93 | CF$_3$, CH$_2$F | CH$_2$FCH$_2$CF$_2$ |
| 94 | CF$_3$, CH$_2$F | CH$_2$FCH$_2$CHF |
| 95 | CF$_3$, CH$_2$F | CH$_3$CF$_2$ |
| 96 | CF$_3$, CH$_2$F | CH$_3$(CF$_2$)$_2$ |
| 97 | CF$_3$, CH$_2$F | CH$_3$CF$_2$CHF |
| 98 | CF$_3$, CH$_2$F | CH$_3$CF$_2$CH$_2$ |
| 99 | CF$_3$, CH$_2$F | CH$_3$CHF |
| 100 | CF$_3$, CH$_2$F | CH$_3$(CHF)$_2$ |
| 101 | CF$_3$, CH$_2$F | CH$_3$CHFCF$_2$ |
| 102 | CF$_3$, CH$_2$F | CH$_3$CHFCH$_2$ |
| 103 | CF$_3$, CH$_2$F | CH$_3$CH$_2$CF$_2$ |
| 104 | CF$_3$, CH$_2$F | CH$_3$CH$_2$(CF$_2$)$_2$ |
| 105 | CF$_3$, CH$_2$F | CH$_3$(CH$_2$)$_2$CF$_2$ |
| 106 | CF$_3$, CH$_2$F | CH$_3$(CH$_2$)$_2$(CF$_2$)$_2$ |
| 107 | CF$_3$, CH$_2$F | CH$_3$(CH$_2$)$_3$CF$_2$ |
| 108 | CF$_3$, CH$_2$F | CH$_3$(CH$_2$)$_3$(CF$_2$)$_2$ |
| 109 | CF$_3$, CH$_3$CF$_2$ | CF$_3$ |
| 110 | CF$_3$, CH$_3$CF$_2$ | CHF$_2$ |
| 111 | CF$_3$, CH$_3$CF$_2$ | CH$_2$F |
| 112 | CF$_3$, CH$_3$CF$_2$ | CH$_3$ |
| 113 | CF$_3$, CH$_3$CF$_2$ | CF$_3$CF$_2$ |
| 114 | CF$_3$, CH$_3$CF$_2$ | CF$_3$(CF$_2$)$_2$ |
| 115 | CF$_3$, CH$_3$CF$_2$ | CF$_3$CF$_2$CHF |
| 116 | CF$_3$, CH$_3$CF$_2$ | CF$_3$CF$_2$CH$_2$ |
| 117 | CF$_3$, CH$_3$CF$_2$ | CF$_3$CHF |
| 118 | CF$_3$, CH$_3$CF$_2$ | CF$_3$(CHF)$_2$ |
| 119 | CF$_3$, CH$_3$CF$_2$ | CF$_3$CHFCF$_2$ |
| 120 | CF$_3$, CH$_3$CF$_2$ | CF$_3$CHFCH$_2$ |
| 121 | CF$_3$, CH$_3$CF$_2$ | CF$_3$CH$_2$ |
| 122 | CF$_3$, CH$_3$CF$_2$ | CF$_3$(CH$_2$)$_2$ |
| 123 | CF$_3$, CH$_3$CF$_2$ | CF$_3$CH$_2$CF$_2$ |
| 124 | CF$_3$, CH$_3$CF$_2$ | CF$_3$CH$_2$CHF |
| 125 | CF$_3$, CH$_3$CF$_2$ | CHF$_2$CF$_2$ |
| 126 | CF$_3$, CH$_3$CF$_2$ | CHF$_2$(CF$_2$)$_2$ |
| 127 | CF$_3$, CH$_3$CF$_2$ | CHF$_2$CF$_2$CHF |
| 128 | CF$_3$, CH$_3$CF$_2$ | CHF$_2$CF$_2$CH$_2$ |
| 129 | CF$_3$, CH$_3$CF$_2$ | CHF$_2$CHF |
| 130 | CF$_3$, CH$_3$CF$_2$ | CHF$_2$(CHF)$_2$ |
| 131 | CF$_3$, CH$_3$CF$_2$ | CHF$_2$CHFCF$_2$ |
| 132 | CF$_3$, CH$_3$CF$_2$ | CHF$_2$CHFCH$_2$ |
| 133 | CF$_3$, CH$_3$CF$_2$ | CHF$_2$CH$_2$ |
| 134 | CF$_3$, CH$_3$CF$_2$ | CHF$_2$(CH$_2$)$_2$ |
| 135 | CF$_3$, CH$_3$CF$_2$ | CHF$_2$CH$_2$CF$_2$ |
| 136 | CF$_3$, CH$_3$CF$_2$ | CHF$_2$CH$_2$CHF |
| 137 | CF$_3$, CH$_3$CF$_2$ | CH$_2$FCF$_2$ |
| 138 | CF$_3$, CH$_3$CF$_2$ | CH$_2$F(CF$_2$)$_2$ |
| 139 | CF$_3$, CH$_3$CF$_2$ | CH$_2$FCF$_2$CHF |
| 140 | CF$_3$, CH$_3$CF$_2$ | CH$_2$FCF$_2$CH$_2$ |
| 141 | CF$_3$, CH$_3$CF$_2$ | CH$_2$FCHF |
| 142 | CF$_3$, CH$_3$CF$_2$ | CH$_2$F(CHF)$_2$ |
| 143 | CF$_3$, CH$_3$CF$_2$ | CH$_2$FCHFCF$_2$ |
| 144 | CF$_3$, CH$_3$CF$_2$ | CH$_2$FCHFCH$_2$ |
| 145 | CF$_3$, CH$_3$CF$_2$ | CH$_2$FCH$_2$ |
| 146 | CF$_3$, CH$_3$CF$_2$ | CH$_2$F(CH$_2$)$_2$ |
| 147 | CF$_3$, CH$_3$CF$_2$ | CH$_2$FCH$_2$CF$_2$ |
| 148 | CF$_3$, CH$_3$CF$_2$ | CH$_2$FCH$_2$CHF |
| 149 | CF$_3$, CH$_3$CF$_2$ | CH$_3$CF$_2$ |
| 150 | CF$_3$, CH$_3$CF$_2$ | CH$_3$(CF$_2$)$_2$ |
| 151 | CF$_3$, CH$_3$CF$_2$ | CH$_3$CF$_2$CHF |
| 152 | CF$_3$, CH$_3$CF$_2$ | CH$_3$CF$_2$CH$_2$ |
| 153 | CF$_3$, CH$_3$CF$_2$ | CH$_3$CHF |
| 154 | CF$_3$, CH$_3$CF$_2$ | CH$_3$(CHF)$_2$ |
| 155 | CF$_3$, CH$_3$CF$_2$ | CH$_3$CHFCF$_2$ |
| 156 | CF$_3$, CH$_3$CF$_2$ | CH$_3$CHFCH$_2$ |
| 157 | CF$_3$, CH$_3$CF$_2$ | CH$_3$CH$_2$CF$_2$ |
| 158 | CF$_3$, CH$_3$CF$_2$ | CH$_3$CH$_2$(CF$_2$)$_2$ |
| 159 | CF$_3$, CH$_3$CF$_2$ | CH$_3$(CH$_2$)$_2$CF$_2$ |
| 160 | CF$_3$, CH$_3$CF$_2$ | CH$_3$(CH$_2$)$_2$(CF$_2$)$_2$ |
| 161 | CF$_3$, CH$_3$CF$_2$ | CH$_3$(CH$_2$)$_3$CF$_2$ |
| 162 | CF$_3$, CH$_3$CF$_2$ | CH$_3$(CH$_2$)$_3$(CF$_2$)$_2$ |
| 163 | CHF$_2$, CH$_2$F | CF$_3$ |
| 164 | CHF$_2$, CH$_2$F | CHF$_2$ |
| 165 | CHF$_2$, CH$_2$F | CH$_2$F |
| 166 | CHF$_2$, CH$_2$F | CH$_3$ |
| 167 | CHF$_2$, CH$_2$F | CF$_3$CF$_2$ |
| 168 | CHF$_2$, CH$_2$F | CF$_3$(CF$_2$)$_2$ |
| 169 | CHF$_2$, CH$_2$F | CF$_3$CF$_2$CHF |
| 170 | CHF$_2$, CH$_2$F | CF$_3$CF$_2$CH$_2$ |
| 171 | CHF$_2$, CH$_2$F | CF$_3$CHF |
| 172 | CHF$_2$, CH$_2$F | CF$_3$(CHF)$_2$ |
| 173 | CHF$_2$, CH$_2$F | CF$_3$CHFCF$_2$ |
| 174 | CHF$_2$, CH$_2$F | CF$_3$CHFCH$_2$ |
| 175 | CHF$_2$, CH$_2$F | CF$_3$CH$_2$ |
| 176 | CHF$_2$, CH$_2$F | CF$_3$(CH$_2$)$_2$ |
| 177 | CHF$_2$, CH$_2$F | CF$_3$CH$_2$CF$_2$ |
| 178 | CHF$_2$, CH$_2$F | CF$_3$CH$_2$CHF |
| 179 | CHF$_2$, CH$_2$F | CHF$_2$CF$_2$ |
| 180 | CHF$_2$, CH$_2$F | CHF$_2$(CF$_2$)$_2$ |
| 181 | CHF$_2$, CH$_2$F | CHF$_2$CF$_2$CHF |
| 182 | CHF$_2$, CH$_2$F | CHF$_2$CF$_2$CH$_2$ |
| 183 | CHF$_2$, CH$_2$F | CHF$_2$CHF |
| 184 | CHF$_2$, CH$_2$F | CHF$_2$(CHF)$_2$ |
| 185 | CHF$_2$, CH$_2$F | CHF$_2$CHFCF$_2$ |
| 186 | CHF$_2$, CH$_2$F | CHF$_2$CHFCH$_2$ |
| 187 | CHF$_2$, CH$_2$F | CHF$_2$CH$_2$ |
| 188 | CHF$_2$, CH$_2$F | CHF$_2$(CH$_2$)$_2$ |
| 189 | CHF$_2$, CH$_2$F | CHF$_2$CH$_2$CF$_2$ |
| 190 | CHF$_2$, CH$_2$F | CHF$_2$CH$_2$CHF |
| 191 | CHF$_2$, CH$_2$F | CH$_2$FCF$_2$ |
| 192 | CHF$_2$, CH$_2$F | CH$_2$F(CF$_2$)$_2$ |
| 193 | CHF$_2$, CH$_2$F | CH$_2$FCF$_2$CHF |
| 194 | CHF$_2$, CH$_2$F | CH$_2$FCF$_2$CH$_2$ |
| 195 | CHF$_2$, CH$_2$F | CH$_2$FCHF |
| 196 | CHF$_2$, CH$_2$F | CH$_2$F(CHF)$_2$ |
| 197 | CHF$_2$, CH$_2$F | CH$_2$FCHFCF$_2$ |
| 198 | CHF$_2$, CH$_2$F | CH$_2$FCHFCH$_2$ |
| 199 | CHF$_2$, CH$_2$F | CH$_2$FCH$_2$ |
| 200 | CHF$_2$, CH$_2$F | CH$_2$F(CH$_2$)$_2$ |
| 201 | CHF$_2$, CH$_2$F | CH$_2$FCH$_2$CF$_2$ |
| 202 | CHF$_2$, CH$_2$F | CH$_2$FCH$_2$CHF |
| 203 | CHF$_2$, CH$_2$F | CH$_3$CF$_2$ |
| 204 | CHF$_2$, CH$_2$F | CH$_3$(CF$_2$)$_2$ |
| 205 | CHF$_2$, CH$_2$F | CH$_3$CF$_2$CHF |
| 206 | CHF$_2$, CH$_2$F | CH$_3$CF$_2$CH$_2$ |
| 207 | CHF$_2$, CH$_2$F | CH$_3$CHF |
| 208 | CHF$_2$, CH$_2$F | CH$_3$(CHF)$_2$ |

TABLE I-continued

| Example | R | R' |
|---|---|---|
| 209 | $CHF_2$, $CH_2F$ | $CH_3CHFCF_2$ |
| 210 | $CHF_2$, $CH_2F$ | $CH_3CHFCH_2$ |
| 211 | $CHF_2$, $CH_2F$ | $CH_3CH_2CF_2$ |
| 212 | $CHF_2$, $CH_2F$ | $CH_3CH_2(CF_2)_2$ |
| 213 | $CHF_2$, $CH_2F$ | $CH_3(CH_2)_2CF_2$ |
| 214 | $CHF_2$, $CH_2F$ | $CH_3(CH_2)_2(CF_2)_2$ |
| 215 | $CHF_2$, $CH_2F$ | $CH_3(CH_2)_3CF_2$ |
| 216 | $CHF_2$, $CH_2F$ | $CH_3(CH_2)_3(CF_2)_2$ |
| 217 | $CHF_2$, $CH_3CF_2$ | $CF_3$ |
| 218 | $CHF_2$, $CH_3CF_2$ | $CHF_2$ |
| 219 | $CHF_2$, $CH_3CF_2$ | $CH_2F$ |
| 220 | $CHF_2$, $CH_3CF_2$ | $CH_3$ |
| 221 | $CHF_2$, $CH_3CF_2$ | $CF_3CF_2$ |
| 222 | $CHF_2$, $CH_3CF_2$ | $CF_3(CF_2)_2$ |
| 223 | $CHF_2$, $CH_3CF_2$ | $CF_3CF_2CHF$ |
| 224 | $CHF_2$, $CH_3CF_2$ | $CF_3CF_2CH_2$ |
| 225 | $CHF_2$, $CH_3CF_2$ | $CF_3CHF$ |
| 226 | $CHF_2$, $CH_3CF_2$ | $CF_3(CHF)_2$ |
| 227 | $CHF_2$, $CH_3CF_2$ | $CF_3CHFCF_2$ |
| 228 | $CHF_2$, $CH_3CF_2$ | $CF_3CHFCH_2$ |
| 229 | $CHF_2$, $CH_3CF_2$ | $CF_3CH_2$ |
| 230 | $CHF_2$, $CH_3CF_2$ | $CF_3(CH_2)_2$ |
| 231 | $CHF_2$, $CH_3CF_2$ | $CF_3CH_2CF_2$ |
| 232 | $CHF_2$, $CH_3CF_2$ | $CF_3CH_2CHF$ |
| 233 | $CHF_2$, $CH_3CF_2$ | $CHF_2CF_2$ |
| 234 | $CHF_2$, $CH_3CF_2$ | $CHF_2(CF_2)_2$ |
| 235 | $CHF_2$, $CH_3CF_2$ | $CHF_2CF_2CHF$ |
| 236 | $CHF_2$, $CH_3CF_2$ | $CHF_2CF_2CH_2$ |
| 237 | $CHF_2$, $CH_3CF_2$ | $CHF_2CHF$ |
| 238 | $CHF_2$, $CH_3CF_2$ | $CHF_2(CHF)_2$ |
| 239 | $CHF_2$, $CH_3CF_2$ | $CHF_2CHFCF_2$ |
| 240 | $CHF_2$, $CH_3CF_2$ | $CHF_2CHFCH_2$ |
| 241 | $CHF_2$, $CH_3CF_2$ | $CHF_2CH_2$ |
| 242 | $CHF_2$, $CH_3CF_2$ | $CHF_2(CH_2)_2$ |
| 243 | $CHF_2$, $CH_3CF_2$ | $CHF_2CH_2CF_2$ |
| 244 | $CHF_2$, $CH_3CF_2$ | $CHF_2CH_2CHF$ |
| 245 | $CHF_2$, $CH_3CF_2$ | $CH_2FCF_2$ |
| 246 | $CHF_2$, $CH_3CF_2$ | $CH_2F(CF_2)_2$ |
| 247 | $CHF_2$, $CH_3CF_2$ | $CH_2FCF_2CHF$ |
| 248 | $CHF_2$, $CH_3CF_2$ | $CH_2FCF_2CH_2$ |
| 249 | $CHF_2$, $CH_3CF_2$ | $CH_2FCHF$ |
| 250 | $CHF_2$, $CH_3CF_2$ | $CH_2F(CHF)_2$ |
| 251 | $CHF_2$, $CH_3CF_2$ | $CH_2FCHFCF_2$ |
| 252 | $CHF_2$, $CH_3CF_2$ | $CH_2FCHFCH_2$ |
| 253 | $CHF_2$, $CH_3CF_2$ | $CH_2FCH_2$ |
| 254 | $CHF_2$, $CH_3CF_2$ | $CH_2F(CH_2)_2$ |
| 255 | $CHF_2$, $CH_3CF_2$ | $CH_2FCH_2CF_2$ |
| 256 | $CHF_2$, $CH_3CF_2$ | $CH_2FCH_2CHF$ |
| 257 | $CHF_2$, $CH_3CF_2$ | $CH_3CF_2$ |
| 258 | $CHF_2$, $CH_3CF_2$ | $CH_3(CF_2)_2$ |
| 259 | $CHF_2$, $CH_3CF_2$ | $CH_3CF_2CHF$ |
| 260 | $CHF_2$, $CH_3CF_2$ | $CH_3CF_2CH_2$ |
| 261 | $CHF_2$, $CH_3CF_2$ | $CH_3CHF$ |
| 262 | $CHF_2$, $CH_3CF_2$ | $CH_3(CHF)_2$ |
| 263 | $CHF_2$, $CH_3CF_2$ | $CH_3CHFCF_2$ |
| 264 | $CHF_2$, $CH_3CF_2$ | $CH_3CHFCH_2$ |
| 265 | $CHF_2$, $CH_3CF_2$ | $CH_3CH_2CF_2$ |
| 266 | $CHF_2$, $CH_3CF_2$ | $CH_3CH_2(CF_2)_2$ |
| 267 | $CHF_2$, $CH_3CF_2$ | $CH_3(CH_2)_2CF_2$ |
| 268 | $CHF_2$, $CH_3CF_2$ | $CH_3(CH_2)_2(CF_2)_2$ |
| 269 | $CHF_2$, $CH_3CF_2$ | $CH_3(CH_2)_3CF_2$ |
| 270 | $CHF_2$, $CH_3CF_2$ | $CH_3(CH_2)_3(CF_2)_2$ |
| 271 | $CH_2F$, $CH_3CF_2$ | $CF_3$ |
| 272 | $CH_2F$, $CH_3CF_2$ | $CHF_2$ |
| 273 | $CH_2F$, $CH_3CF_2$ | $CH_2F$ |
| 274 | $CH_2F$, $CH_3CF_2$ | $CH_3$ |
| 275 | $CH_2F$, $CH_3CF_2$ | $CF_3CF_2$ |
| 276 | $CH_2F$, $CH_3CF_2$ | $CF_3(CF_2)_2$ |
| 277 | $CH_2F$, $CH_3CF_2$ | $CF_3CF_2CHF$ |
| 278 | $CH_2F$, $CH_3CF_2$ | $CF_3CF_2CH_2$ |
| 279 | $CH_2F$, $CH_3CF_2$ | $CF_3CHF$ |
| 280 | $CH_2F$, $CH_3CF_2$ | $CF_3(CHF)_2$ |
| 281 | $CH_2F$, $CH_3CF_2$ | $CF_2CHFCF_2$ |
| 282 | $CH_2F$, $CH_3CF_2$ | $CF_3CHFCH_2$ |
| 283 | $CH_2F$, $CH_3CF_2$ | $CF_3CH_2$ |
| 284 | $CH_2F$, $CH_3CF_2$ | $CF_3(CH_2)_2$ |
| 285 | $CH_2F$, $CH_3CF_2$ | $CF_3CH_2CF_2$ |
| 286 | $CH_2F$, $CH_3CF_2$ | $CF_3CH_2CHF$ |
| 287 | $CH_2F$, $CH_3CF_2$ | $CHF_2CF_2$ |
| 288 | $CH_2F$, $CH_3CF_2$ | $CHF_2(CF_2)_2$ |
| 289 | $CH_2F$, $CH_3CF_2$ | $CHF_2CF_2CHF$ |
| 290 | $CH_2F$, $CH_3CF_2$ | $CHF_2CF_2CH_2$ |
| 291 | $CH_2F$, $CH_3CF_2$ | $CHF_2CHF$ |
| 292 | $CH_2F$, $CH_3CF_2$ | $CHF_2(CHF)_2$ |
| 293 | $CH_2F$, $CH_3CF_2$ | $CHF_2CHFCF_2$ |
| 294 | $CH_2F$, $CH_3CF_2$ | $CHF_2CHFCH_2$ |
| 295 | $CH_2F$, $CH_3CF_2$ | $CHF_2CH_2$ |
| 296 | $CH_2F$, $CH_3CF_2$ | $CHF_2(CH_2)_2$ |
| 297 | $CH_2F$, $CH_3CF_2$ | $CHF_2CH_2CF_2$ |
| 298 | $CH_2F$, $CH_3CF_2$ | $CHF_2CH_2CHF$ |
| 299 | $CH_2F$, $CH_3CF_2$ | $CH_2FCF_2$ |
| 300 | $CH_2F$, $CH_3CF_2$ | $CH_2F(CF_2)_2$ |
| 301 | $CH_2F$, $CH_3CF_2$ | $CH_2FCF_2CHF$ |
| 302 | $CH_2F$, $CH_3CF_2$ | $CH_2FCF_2CH_2$ |
| 303 | $CH_2F$, $CH_3CF_2$ | $CH_2FCHF$ |
| 304 | $CH_2F$, $CH_3CF_2$ | $CH_2F(CHF)_2$ |
| 305 | $CH_2F$, $CH_3CF_2$ | $CH_2FCHFCF_2$ |
| 306 | $CH_2F$, $CH_3CF_2$ | $CH_2FCHFCH_2$ |
| 307 | $CH_2F$, $CH_3CF_2$ | $CH_2FCH_2$ |
| 308 | $CH_2F$, $CH_3CF_2$ | $CH_2F(CH_2)_2$ |
| 309 | $CH_2F$, $CH_3CF_2$ | $CH_2FCH_2CF_2$ |
| 310 | $CH_2F$, $CH_3CF_2$ | $CH_2FCH_2CHF$ |
| 311 | $CH_2F$, $CH_3CF_2$ | $CH_3CF_2$ |
| 312 | $CH_2F$, $CH_3CF_2$ | $CH_3(CF_2)_2$ |
| 313 | $CH_2F$, $CH_3CF_2$ | $CH_3CF_2CHF$ |
| 314 | $CH_2F$, $CH_3CF_2$ | $CH_3CF_2CH_2$ |
| 315 | $CH_2F$, $CH_3CF_2$ | $CH_3CHF$ |
| 316 | $CH_2F$, $CH_3CF_2$ | $CH_3(CHF)_2$ |
| 317 | $CH_2F$, $CH_3CF_2$ | $CH_3CHFCF_2$ |
| 318 | $CH_2F$, $CH_3CF_2$ | $CH_3CHFCH_2$ |
| 319 | $CH_2F$, $CH_3CF_2$ | $CH_3CH_2CF_2$ |
| 320 | $CH_2F$, $CH_3CF_2$ | $CH_3CH_2(CF_2)_2$ |
| 321 | $CH_2F$, $CH_3CF_2$ | $CH_3(CH_2)_2CF_2$ |
| 322 | $CH_2F$, $CH_3CF_2$ | $CH_3(CH_2)_2(CF_2)_2$ |
| 323 | $CH_2F$, $CH_3CF_2$ | $CH_3(CH_2)_3CF_2$ |
| 324 | $CH_2F$, $CH_3CF_2$ | $CH_3(CH_2)_3(CF_2)_2$ |
| 325 | $CF_3$, $CF_3$ | $CF_3$ |
| 326 | $CF_3$, $CF_3$ | $CHF_2$ |
| 327 | $CF_3$, $CF_3$ | $CH_2F$ |
| 328 | $CF_3$, $CF_3$ | $CH_3$ |
| 329 | $CF_3$, $CF_3$ | $CF_3CF_2$ |
| 330 | $CF_3$, $CF_3$ | $CF_3(CF_2)_2$ |
| 331 | $CF_3$, $CF_3$ | $CF_3CF_2CHF$ |
| 332 | $CF_3$, $CF_3$ | $CF_3CF_2CH_2$ |
| 333 | $CF_3$, $CF_3$ | $CF_3CHF$ |
| 334 | $CF_3$, $CF_3$ | $CF_3(CHF)_2$ |
| 335 | $CF_3$, $CF_3$ | $CF_3CHFCF_2$ |
| 336 | $CF_3$, $CF_3$ | $CF_3CHFCH_2$ |
| 337 | $CF_3$, $CF_3$ | $CF_3CH_2$ |
| 338 | $CF_3$, $CF_3$ | $CF_3(CH_2)_2$ |
| 339 | $CF_3$, $CF_3$ | $CF_3CH_2CF_2$ |
| 340 | $CF_3$, $CF_3$ | $CF_3CH_2CHF$ |
| 341 | $CF_3$, $CF_3$ | $CHF_2CF_2$ |
| 342 | $CF_3$, $CF_3$ | $CHF_2(CF_2)_2$ |
| 343 | $CF_3$, $CF_3$ | $CHF_2CF_2CHF$ |
| 344 | $CF_3$, $CF_3$ | $CHF_2CF_2CH_2$ |
| 345 | $CF_3$, $CF_3$ | $CHF_2CHF$ |
| 346 | $CF_3$, $CF_3$ | $CHF_2(CHF)_2$ |
| 347 | $CF_3$, $CF_3$ | $CHF_2CHFCF_2$ |
| 348 | $CF_3$, $CF_3$ | $CHF_2CHFCH_2$ |
| 349 | $CF_3$, $CF_3$ | $CHF_2CH_2$ |
| 350 | $CF_3$, $CF_3$ | $CHF_2(CH_2)_2$ |
| 351 | $CF_3$, $CF_3$ | $CHF_2CH_2CF_2$ |
| 352 | $CF_3$, $CF_3$ | $CHF_2CH_2CHF$ |
| 353 | $CF_3$, $CF_3$ | $CH_2FCF_2$ |
| 354 | $CF_3$, $CF_3$ | $CH_2F(CF_2)_2$ |
| 355 | $CF_3$, $CF_3$ | $CH_2FCF_2CHF$ |
| 356 | $CF_3$, $CF_3$ | $CH_2FCF_2CH_2$ |
| 357 | $CF_3$, $CF_3$ | $CH_2FCHF$ |
| 358 | $CF_3$, $CF_3$ | $CH_2F(CHF)_2$ |
| 359 | $CF_3$, $CF_3$ | $CH_2FCHFCF_2$ |
| 360 | $CF_3$, $CF_3$ | $CH_2FCHFCH_2$ |
| 361 | $CF_3$, $CF_3$ | $CH_2FCH_2$ |
| 362 | $CF_3$, $CF_3$ | $CH_2F(CH_2)_2$ |
| 363 | $CF_3$, $CF_3$ | $CH_2FCH_2CF_2$ |
| 364 | $CF_3$, $CF_3$ | $CH_2FCH_2CHF$ |
| 365 | $CF_3$, $CF_3$ | $CH_3CF_2$ |
| 366 | $CF_3$, $CF_3$ | $CH_3(CF_2)_2$ |
| 367 | $CF_3$, $CF_3$ | $CH_3CF_2CHF$ |
| 368 | $CF_3$, $CF_3$ | $CH_3CF_2CH_2$ |
| 369 | $CF_3$, $CF_3$ | $CH_3CHF$ |
| 370 | $CF_3$, $CF_3$ | $CH_3(CHF)_2$ |

TABLE I-continued

| Example | R | R' |
|---|---|---|
| 371 | CF$_3$, CF$_3$ | CH$_3$CHFCF$_2$ |
| 372 | CF$_3$, CF$_3$ | CH$_3$CHFCH$_2$ |
| 373 | CF$_3$, CF$_3$ | CH$_3$CH$_2$CF$_2$ |
| 374 | CF$_3$, CF$_3$ | CH$_3$CH$_2$(CF$_2$)$_2$ |
| 375 | CF$_3$, CF$_3$ | CH$_3$(CH$_2$)$_2$CF$_2$ |
| 376 | CF$_3$, CF$_3$ | CH$_3$(CH$_2$)$_2$(CF$_2$)$_2$ |
| 377 | CF$_3$, CF$_3$ | CH$_3$(CH$_2$)$_3$CF$_2$ |
| 378 | CF$_3$, CF$_3$ | CH$_3$(CH$_2$)$_3$(CF$_2$)$_2$ |
| 379 | CHF$_2$, CHF$_2$ | CF$_3$ |
| 380 | CHF$_2$, CHF$_2$ | CHF$_2$ |
| 381 | CHF$_2$, CHF$_2$ | CH$_2$F |
| 382 | CHF$_2$, CHF$_2$ | CH$_3$ |
| 383 | CHF$_2$, CHF$_2$ | CF$_3$CF$_2$ |
| 384 | CHF$_2$, CHF$_2$ | CF$_3$(CF$_2$)$_2$ |
| 385 | CHF$_2$, CHF$_2$ | CF$_3$CF$_2$CHF |
| 386 | CHF$_2$, CHF$_2$ | CF$_3$CF$_2$CH$_2$ |
| 387 | CHF$_2$, CHF$_2$ | CF$_3$CHF |
| 388 | CHF$_2$, CHF$_2$ | CF$_3$(CHF)$_2$ |
| 389 | CHF$_2$, CHF$_2$ | CF$_3$CHFCF$_2$ |
| 390 | CHF$_2$, CHF$_2$ | CF$_3$CHFCH$_2$ |
| 391 | CHF$_2$, CHF$_2$ | CF$_3$CH$_2$ |
| 392 | CHF$_2$, CHF$_2$ | CF$_3$(CH$_2$)$_2$ |
| 393 | CHF$_2$, CHF$_2$ | CF$_3$CH$_2$CF$_2$ |
| 394 | CHF$_2$, CHF$_2$ | CF$_3$CH$_2$CHF |
| 395 | CHF$_2$, CHF$_2$ | CHF$_2$CF$_2$ |
| 396 | CHF$_2$, CHF$_2$ | CHF$_2$(CF$_2$)$_2$ |
| 397 | CHF$_2$, CHF$_2$ | CHF$_2$CF$_2$CHF |
| 398 | CHF$_2$, CHF$_2$ | CHF$_2$CF$_2$CH$_2$ |
| 399 | CHF$_2$, CHF$_2$ | CHF$_2$CHF |
| 400 | CHF$_2$, CHF$_2$ | CHF$_2$(CHF)$_2$ |
| 401 | CHF$_2$, CHF$_2$ | CHF$_2$CHFCF$_2$ |
| 402 | CHF$_2$, CHF$_2$ | CHF$_2$CHFCH$_2$ |
| 403 | CHF$_2$, CHF$_2$ | CHF$_2$CH$_2$ |
| 404 | CHF$_2$, CHF$_2$ | CHF$_2$(CH$_2$)$_2$ |
| 405 | CHF$_2$, CHF$_2$ | CHF$_2$CH$_2$CF$_2$ |
| 406 | CHF$_2$, CHF$_2$ | CHF$_2$CH$_2$CHF |
| 407 | CHF$_2$, CHF$_2$ | CH$_2$FCF$_2$ |
| 408 | CHF$_2$, CHF$_2$ | CH$_2$F(CF$_2$)$_2$ |
| 409 | CHF$_2$, CHF$_2$ | CH$_2$FCF$_2$CHF |
| 410 | CHF$_2$, CHF$_2$ | CH$_2$FCF$_2$CH$_2$ |
| 411 | CHF$_2$, CHF$_2$ | CH$_2$FCHF |
| 412 | CHF$_2$, CHF$_2$ | CH$_2$F(CHF)$_2$ |
| 413 | CHF$_2$, CHF$_2$ | CH$_2$FCHFCF$_2$ |
| 414 | CHF$_2$, CHF$_2$ | CH$_2$FCHFCH$_2$ |
| 415 | CHF$_2$, CHF$_2$ | CH$_2$FCH$_2$ |
| 416 | CHF$_2$, CHF$_2$ | CH$_2$F(CH$_2$)$_2$ |
| 417 | CHF$_2$, CHF$_2$ | CH$_2$FCH$_2$CF$_2$ |
| 418 | CHF$_2$, CHF$_2$ | CH$_2$FCH$_2$CHF |
| 419 | CHF$_2$, CHF$_2$ | CH$_3$CF$_2$ |
| 420 | CHF$_2$, CHF$_2$ | CH$_3$(CF$_2$)$_2$ |
| 421 | CHF$_2$, CHF$_2$ | CH$_3$CF$_2$CHF |
| 422 | CHF$_2$, CHF$_2$ | CH$_3$CF$_2$CH$_2$ |
| 423 | CHF$_2$, CHF$_2$ | CH$_3$CHF |
| 424 | CHF$_2$, CHF$_2$ | CH$_3$(CHF)$_2$ |
| 425 | CHF$_2$, CHF$_2$ | CH$_3$CHFCF$_2$ |
| 426 | CHF$_2$, CHF$_2$ | CH$_3$CHFCH$_2$ |
| 427 | CHF$_2$, CHF$_2$ | CH$_3$CH$_2$CF$_2$ |
| 428 | CHF$_2$, CHF$_2$ | CH$_3$CH$_2$(CF$_2$)$_2$ |
| 429 | CHF$_2$, CHF$_2$ | CH$_3$(CH$_2$)$_2$CF$_2$ |
| 430 | CHF$_2$, CHF$_2$ | CH$_3$(CH$_2$)$_2$(CF$_2$)$_2$ |
| 431 | CHF$_2$, CHF$_2$ | CH$_3$(CH$_2$)$_3$CF$_2$ |
| 432 | CHF$_2$, CHF$_2$ | CH$_3$(CH$_2$)$_3$(CF$_2$)$_2$ |
| 433 | CH$_2$F, CH$_2$F | CF$_3$ |
| 434 | CH$_2$F, CH$_2$F | CHF$_2$ |
| 435 | CH$_2$F, CH$_2$F | CH$_2$F |
| 436 | CH$_2$F, CH$_2$F | CH$_3$ |
| 437 | CH$_2$F, CH$_2$F | CF$_3$CF$_2$ |
| 438 | CH$_2$F, CH$_2$F | CF$_3$(CF$_2$)$_2$ |
| 439 | CH$_2$F, CH$_2$F | CF$_3$CF$_2$CHF |
| 440 | CH$_2$F, CH$_2$F | CF$_3$CF$_2$CH$_2$ |
| 441 | CH$_2$F, CH$_2$F | CF$_3$CHF |
| 442 | CH$_2$F, CH$_2$F | CF$_3$(CHF)$_2$ |
| 443 | CH$_2$F, CH$_2$F | CF$_3$CHFCF$_2$ |
| 444 | CH$_2$F, CH$_2$F | CF$_3$CHFCH$_2$ |
| 445 | CH$_2$F, CH$_2$F | CF$_3$CH$_2$ |
| 446 | CH$_2$F, CH$_2$F | CF$_3$(CH$_2$)$_2$ |
| 447 | CH$_2$F, CH$_2$F | CF$_3$CH$_2$CF$_2$ |
| 448 | CH$_2$F, CH$_2$F | CF$_3$CH$_2$CHF |
| 449 | CH$_2$F, CH$_2$F | CHF$_2$CF$_2$ |
| 450 | CH$_2$F, CH$_2$F | CHF$_2$(CF$_2$)$_2$ |
| 451 | CH$_2$F, CH$_2$F | CHF$_2$CF$_2$CHF |
| 452 | CH$_2$F, CH$_2$F | CHF$_2$CF$_2$CH$_2$ |
| 453 | CH$_2$F, CH$_2$F | CHF$_2$CHF |
| 454 | CH$_2$F, CH$_2$F | CHF$_2$(CHF)$_2$ |
| 455 | CH$_2$F, CH$_2$F | CHF$_2$CHFCF$_2$ |
| 456 | CH$_2$F, CH$_2$F | CHF$_2$CHFCH$_2$ |
| 457 | CH$_2$F, CH$_2$F | CHF$_2$CH$_2$ |
| 458 | CH$_2$F, CH$_2$F | CHF$_2$(CH$_2$)$_2$ |
| 459 | CH$_2$F, CH$_2$F | CHF$_2$CH$_2$CF$_2$ |
| 460 | CH$_2$F, CH$_2$F | CHF$_2$CH$_2$CHF |
| 461 | CH$_2$F, CH$_2$F | CH$_2$FCF$_2$ |
| 462 | CH$_2$F, CH$_2$F | CH$_2$F(CF$_2$)$_2$ |
| 463 | CH$_2$F, CH$_2$F | CH$_2$FCF$_2$CHF |
| 464 | CH$_2$F, CH$_2$F | CH$_2$FCF$_2$CH$_2$ |
| 465 | CH$_2$F, CH$_2$F | CH$_2$FCHF |
| 466 | CH$_2$F, CH$_2$F | CH$_2$F(CHF)$_2$ |
| 467 | CH$_2$F, CH$_2$F | CH$_2$FCHFCF$_2$ |
| 468 | CH$_2$F, CH$_2$F | CH$_2$FCHFCH$_2$ |
| 469 | CH$_2$F, CH$_2$F | CH$_2$FCH$_2$ |
| 470 | CH$_2$F, CH$_2$F | CH$_2$F(CH$_2$)$_2$ |
| 471 | CH$_2$F, CH$_2$F | CH$_2$FCH$_2$CF$_2$ |
| 472 | CH$_2$F, CH$_2$F | CH$_2$FCH$_2$CHF |
| 473 | CH$_2$F, CH$_2$F | CH$_3$CF$_2$ |
| 474 | CH$_2$F, CH$_2$F | CH$_3$(CF$_2$)$_2$ |
| 475 | CH$_2$F, CH$_2$F | CH$_3$CF$_2$CHF |
| 476 | CH$_2$F, CH$_2$F | CH$_3$CF$_2$CH$_2$ |
| 477 | CH$_2$F, CH$_2$F | CH$_3$CHF |
| 478 | CH$_2$F, CH$_2$F | CH$_3$(CHF)$_2$ |
| 479 | CH$_2$F, CH$_2$F | CH$_3$CHFCF$_2$ |
| 480 | CH$_2$F, CH$_2$F | CH$_3$CHFCH$_2$ |
| 481 | CH$_2$F, CH$_2$F | CH$_3$CH$_2$CF$_2$ |
| 482 | CH$_2$F, CH$_2$F | CH$_3$CH$_2$(CF$_2$)$_2$ |
| 483 | CH$_2$F, CH$_2$F | CH$_3$(CH$_2$)$_2$CF$_2$ |
| 484 | CH$_2$F, CH$_2$F | CH$_3$(CH$_2$)$_2$(CF$_2$)$_2$ |
| 485 | CH$_2$F, CH$_2$F | CH$_3$(CH$_2$)$_3$CF$_2$ |
| 486 | CH$_2$F, CH$_2$F | CH$_3$(CH$_2$)$_3$(CF$_2$)$_2$ |
| 487 | CH$_3$CF$_2$, CH$_3$CF$_2$ | CF$_3$ |
| 488 | CH$_3$CF$_2$, CH$_3$CF$_2$ | CHF$_2$ |
| 489 | CH$_3$CF$_2$, CH$_3$CF$_2$ | CH$_2$F |
| 490 | CH$_3$CF$_2$, CH$_3$CF$_2$ | CH$_3$ |
| 491 | CH$_3$CF$_2$, CH$_3$CF$_2$ | CF$_3$CF$_2$ |
| 492 | CH$_3$CF$_2$, CH$_3$CF$_2$ | CF$_3$(CF$_2$)$_2$ |
| 493 | CH$_3$CF$_2$, CH$_3$CF$_2$ | CF$_3$CF$_2$CHF |
| 494 | CH$_3$CF$_2$, CH$_3$CF$_2$ | CF$_3$CF$_2$CH$_2$ |
| 495 | CH$_3$CF$_2$, CH$_3$CF$_2$ | CF$_3$CHF |
| 496 | CH$_3$CF$_2$, CH$_3$CF$_2$ | CF$_3$(CHF)$_2$ |
| 497 | CH$_3$CF$_2$, CH$_3$CF$_2$ | CF$_3$CHFCF$_2$ |
| 498 | CH$_3$CF$_2$, CH$_3$CF$_2$ | CF$_3$CHFCH$_2$ |
| 499 | CH$_3$CF$_2$, CH$_3$CF$_2$ | CF$_3$CH$_2$ |
| 500 | CH$_3$CF$_2$, CH$_3$CF$_2$ | CF$_3$(CH$_2$)$_2$ |
| 501 | CH$_3$CF$_2$, CH$_3$CF$_2$ | CF$_3$CH$_2$CF$_2$ |
| 502 | CH$_3$CF$_2$, CH$_3$CF$_2$ | CF$_3$CH$_2$CHF |
| 503 | CH$_3$CF$_2$, CH$_3$CF$_2$ | CHF$_2$CF$_2$ |
| 504 | CH$_3$CF$_2$, CH$_3$CF$_2$ | CHF$_2$(CF$_2$)$_2$ |
| 505 | CH$_3$CF$_2$, CH$_3$CF$_2$ | CHF$_2$CF$_2$CHF |
| 506 | CH$_3$CF$_2$, CH$_3$CF$_2$ | CHF$_2$CF$_2$CH$_2$ |
| 507 | CH$_3$CF$_2$, CH$_3$CF$_2$ | CHF$_2$CHF |
| 508 | CH$_3$CF$_2$, CH$_3$CF$_2$ | CHF$_2$(CHF)$_2$ |
| 509 | CH$_3$CF$_2$, CH$_3$CF$_2$ | CHF$_2$CHFCF$_2$ |
| 510 | CH$_3$CF$_2$, CH$_3$CF$_2$ | CHF$_2$CHFCH$_2$ |
| 511 | CH$_3$CF$_2$, CH$_3$CF$_2$ | CHF$_2$CH$_2$ |
| 512 | CH$_3$CF$_2$, CH$_3$CF$_2$ | CHF$_2$(CH$_2$)$_2$ |
| 513 | CH$_3$CF$_2$, CH$_3$CF$_2$ | CHF$_2$CH$_2$CF$_2$ |
| 514 | CH$_3$CF$_2$, CH$_3$CF$_2$ | CHF$_2$CH$_2$CHF |
| 515 | CH$_3$CF$_2$, CH$_3$CF$_2$ | CH$_2$FCF$_2$ |
| 516 | CH$_3$CF$_2$, CH$_3$CF$_2$ | CH$_2$F(CF$_2$)$_2$ |
| 517 | CH$_3$CF$_2$, CH$_3$CF$_2$ | CH$_2$FCF$_2$CHF |
| 518 | CH$_3$CF$_2$, CH$_3$CF$_2$ | CH$_2$FCF$_2$CH$_2$ |
| 519 | CH$_3$CF$_2$, CH$_3$CF$_2$ | CH$_2$FCHF |
| 520 | CH$_3$CF$_2$, CH$_3$CF$_2$ | CH$_2$F(CHF)$_2$ |
| 521 | CH$_3$CF$_2$, CH$_3$CF$_2$ | CH$_2$FCHFCF$_2$ |
| 522 | CH$_3$CF$_2$, CH$_3$CF$_2$ | CH$_2$FCHFCH$_2$ |
| 523 | CH$_3$CF$_2$, CH$_3$CF$_2$ | CH$_2$FCH$_2$ |
| 524 | CH$_3$CF$_2$, CH$_3$CF$_2$ | CH$_2$F(CH$_2$)$_2$ |
| 525 | CH$_3$CF$_2$, CH$_3$CF$_2$ | CH$_2$FCH$_2$CF$_2$ |
| 526 | CH$_3$CF$_2$, CH$_3$CF$_2$ | CH$_2$FCH$_2$CHF |
| 527 | CH$_3$CF$_2$, CH$_3$CF$_2$ | CH$_3$CF$_2$ |
| 528 | CH$_3$CF$_2$, CH$_3$CF$_2$ | CH$_3$(CF$_2$)$_2$ |
| 529 | CH$_3$CF$_2$, CH$_3$CF$_2$ | CH$_3$CF$_2$CHF |
| 530 | CH$_3$CF$_2$, CH$_3$CF$_2$ | CH$_3$CF$_2$CH$_2$ |
| 531 | CH$_3$CF$_2$, CH$_3$CF$_2$ | CH$_3$CHF |
| 532 | CH$_3$CF$_2$, CH$_3$CF$_2$ | CH$_3$(CHF)$_2$ |

TABLE I-continued

| Example | R | R' |
|---|---|---|
| 533 | CH₃CF₂, CH₃CF₂ | CH₃CHFCF₂ |
| 534 | CH₃CF₂, CH₃CF₂ | CH₃CHFCH₂ |
| 535 | CH₃CF₂, CH₃CF₂ | CH₃CH₂CF₂ |
| 536 | CH₃CF₂, CH₃CF₂ | CH₃CH₂(CF₂)₂ |
| 537 | CH₃CF₂, CH₃CF₂ | CH₃(CH₂)₂CF₂ |
| 538 | CH₃CF₂, CH₃CF₂ | CH₃(CH₂)₂(CF₂)₂ |
| 539 | CH₃CF₂, CH₃CF₂ | CH₃(CH₂)₃CF₂ |
| 540 | CH₃CF₂, CH₃CF₂ | CH₃(CH₂)₃(CF₂)₂ |

EXAMPLES 541–1,080

Metal coupons are soiled with various types of oil. The soiled metal coupons are immersed in the novel solvents of Table I above for a period of 15 seconds to 2 minutes, removed, and allowed to air dry. Upon visual inspection, the soil appears to be substantially removed.

EXAMPLES 1,081–1,620

Metal coupons are soiled with various types of oil. The soiled metal coupons are wiped with the novel solvents of Table I above and allowed to air dry. Upon visual inspection, the soil appears to be substantially removed.

Having described the invention in detail and by reference to preferred embodiments thereof, it will be t that modifications and variations are possible without departing from the scope of the invention defined in the appended claims.

What is claimed is:

1. A method of cleaning a solid surface having contaminants thereon which comprises the steps of: said surface with a compound having the formula

wherein each R is the same or different and is selected from the group consisting of CF₃, CHF₂, CH₂F, and CH₃CF₂, and R' is an alkyl or fluoroalkyl group having 1 to 6 carbon atoms and (B) substantially removing said contaminants and said compound from said surface.

2. The method of claim 1 wherein said R' is selected from the group consisting of CF₃, CHF₂, CH₂F, CH₃, CF₃(CF₂)ₙ—, CF₃CF₂CHF—, CF₃CF₂CH₂—, CF₃(CHF)ₙ—, CF₃CHFCF₂—, CF₃CHFCH₂—, CF₃(CH₂)ₙ—, CF₃CH₂CF₂—, CF₃CH₂CHF—, CHF₃(CF₂)ₙ—, CHF₂CF₂CHF—, CHF₂CF₂CH₂—, CHF₂(CHF)ₙa—, CHF₂CHFCF₂—, CHF₂CHFCH₂—, CHF₂(CH₂)ₙ—, CHF₂CH₂CF₂—, CHF₂CH₂CHF—, CH₂F(CF₂)ₙ—, CH₂FCF₂CHF—, CH₂FCF₂CH₂—, CH₂F(CHF)ₙ—, CH₂FCHFCF₂—, CH₂FCHFCH₂—, CH₂F(CH₂)ₙ—, CH₂FCH₂CF₂—, CH₂FCH₂CHF—, CH₃(CF₂)ₙ—, CH₃CF₂CHF—, CH₃CF₂CH₂—, CH₃(CHF)ₙ—, CH₃CHFCF₂—, CH₃CHFCH₂—, and CH₃(CH₂)ₘ(CF₂)ₙ, and m is 1 to 3, and n is 1 or 2.

3. The method of claim 1 wherein each of said R is the same.

4. The method of claim 3 wherein each of said R is CF₃.

5. The method of claim 4 wherein said R' is selected from the group consisting of CHF₂, CH₃, and CF₃CH₂—.

6. The method of claim 5 wherein said R' is CHF₂.

7. The method of claim 5 wherein said R' is CH₃.

8. The method of claim 5 wherein said R' is CF₃CH₂—.

9. The method of claim 4 wherein said R' is CF₃CF₂—.

10. The method of claim 1 wherein said compound is selected from the group consisting of 2-difluoromethyl-1,1,3,3-tetrafluoropropane, 2-fluoromethyl-1,3-difluoropropane, and 3-trifluoromethyl-2,2,4,4-tetrafluoropentane.

11. The method of claim 4 wherein said R' is selected from the group consisting of CH₃CF₂—, CH₃(CF₂)₂—, and CH₃CH₂CF₂—.

12. The method of claim 4 wherein said R' is CH₃CF₂—.

13. The method of claim 4 wherein said R' is CH₃(CF₂)₂—.

14. The method of claim 4 wherein said R' is CH₃CH₂CF₂—.